United States Patent [19]

Gundersen

[11] Patent Number: 5,393,525
[45] Date of Patent: Feb. 28, 1995

[54] CONTRAST MEDIUM COMPRISING SUPERPARAMAGNETIC OR FERROMAGNETIC PARTICLES CAPABLE OF INCREASING VISCOSITY AFTER ADMINISTRATION

[75] Inventor: Helge G. Gundersen, Oslo, Norway

[73] Assignee: Nycomed Imaging AS, Oslo, Norway

[21] Appl. No.: 210,738

[22] Filed: Mar. 21, 1994

Related U.S. Application Data

[63] Continuation of Ser. No. 820,642, Jan. 21, 1992, abandoned.

[30] Foreign Application Priority Data

Jul. 21, 1989 [GB] United Kingdom ............... 8916780

[51] Int. Cl.$^6$ .................. A61B 5/055; A61K 9/16; A61K 33/26
[52] U.S. Cl. ........................... 424/9; 424/493; 424/494; 424/646; 424/648; 128/653.4; 436/173
[58] Field of Search ............ 424/9, 4, 457, 460, 424/461, 462, 468, 469, 646, 648, 493, 494; 514/960, 964; 128/653.4, 654; 436/173

[56] References Cited

U.S. PATENT DOCUMENTS

| | | | |
|---|---|---|---|
| 4,610,870 | 9/1986 | Jain et al. | 424/19 |
| 4,729,892 | 3/1988 | Beall | 424/9 |
| 4,770,183 | 9/1988 | Groman et al. | 128/654 |
| 4,863,715 | 9/1989 | Jacobsen et al. | 424/9 |
| 5,069,216 | 12/1991 | Groman et al. | 128/653.4 |
| 5,120,527 | 6/1992 | Li et al. | 424/9 |
| 5,122,363 | 6/1992 | Balkus et al. | 424/9 |
| 5,128,121 | 7/1992 | Berg et al. | 424/9 |
| 5,174,987 | 12/1992 | Takaichi et al. | 424/9 |

FOREIGN PATENT DOCUMENTS

| | | |
|---|---|---|
| 0124766 | 11/1984 | European Pat. Off. |
| 0184899 | 6/1986 | European Pat. Off. |
| 0186947 | 7/1986 | European Pat. Off. |
| WO8504330 | 10/1985 | WIPO |

OTHER PUBLICATIONS

Vinocur, *Diagnostic Imaging*, Apr. 1986, p. 70.
Tiling et al., Society of Magnetic Resonance in Medicine Seventh Annual Meeting and Exhibition, Aug. 20–26, 1988, San Francisco, p. 686.
Parikh, Society of Magnetic Resonance in Medicine Seventh Annual Meeting and Exhibition, Aug. 20–26, 1988, San Francisco, p. 520.
Listinsky et al., Society of Magnetic Resonance in Medicine Seventh Annual Meeting and Exhibition, Aug. 20–26, 1988, San Francisco, p. 525.
Chen et al., Society of Magnetic Resonance in Medicine Seventh Annual Meeting and Exhibition, Aug. 20–26, 1988, San Francisco, p. 733.
Kornmesser et al., *Fortschr. Rontgenstr.*, 147, 5, 1987, 550–556.

*Primary Examiner*—Gary E. Hollinden
*Attorney, Agent, or Firm*—Bacon & Thomas

[57] ABSTRACT

There is provided a contrast medium composition comprising magnetically responsive particles and a physiologically tolerable, incompletely hydrated viscosity enhancing agent.

12 Claims, No Drawings

CONTRAST MEDIUM COMPRISING SUPERPARAMAGNETIC OR FERROMAGNETIC PARTICLES CAPABLE OF INCREASING VISCOSITY AFTER ADMINISTRATION

This application is a Continuation of application Ser. No. 07/820,642, filed Jan. 21, 1992, now abandoned.

The present invention relates to improvements in and relating to magnetic resonance imaging (MRI) and in particular to compositions for use as or in the preparation of MRI contrast media for imaging of the gastrointestinal system or of other body cavities from which contrast media may be discharged from the body without passing through body tissue.

MRI is now well established as a medical diagnostic tool. The ability of the technique to generate high quality images and to differentiate between soft tissues without requiring the patient to be exposed to ionizing radiation has contributed to this success.

Although MRI can be performed without using added contrast media, it has been found that substances which affect the nuclear spin reequilibration of the nuclei (hereinafter the "imaging nuclei"—generally water protons in body fluids and tissues) responsible for the magnetic resonance (MR) signals from which the images are generated may be used to enhance image contrast and, accordingly, in recent years, many such materials have been suggested as MRI contrast agents.

While MRI has until now mainly been used for imaging the central nervous system, the technique has great potential for the imaging of externally voided body cavities, in particular the gastrointestinal (GI) tract. However, development of MRI as a technique for imaging the GI tract, or indeed the abdomen in general, has been hindered by the special problems of imaging the abdomen in which natural inter-tissue contrast is relatively poor, and (although MRI can be performed without the use of added contrast media) by the absence of a particularly effective contrast medium. In particular, there is a need for an improved intraluminal contrast medium (see Vinocur, Diagnostic Imaging, April 1986, page 70).

One important factor contributing to the problems of imaging the GI tract is that for the bowel loops, unlike other body organs, the MR signal intensity varies significantly and unpredictably due to variations in bowel content, incompletely filled bowel loops, the occurrence of gas pockets, absorption and secretion of water, etc. Moreover, the relatively long time periods required for generating an MR image also make the technique vulnerable to physical movements in the region being imaged. While movements of the heart and respiratory system also occur within the same time periods, these movements are periodic and may be compensated for by cardiac and respiratory gating. Movements of the gut however are less predictable and can thus cause problems in the generation of satisfactory MR images.

Several MRI contrast media have been proposed for imaging of the GI tract. (See Tiling et al., Parikh et al., Listinsky et at., and Chen et al., Society of Magnetic Resonance in Medicine (SMRM), San Francisco 1988, Abstracts pages 686, 520, 525 and 733 respectively).

One suggestion has been the use of "positive" contrast agents, that is paramagnetic compounds which shorten the spin-lattice relaxation time (T1) of the imaging nuclei and so result in an increase in image intensity in the body regions into which they distribute. One such positive contrast agent is Gd DTPA and its use in MRI of the GI tract is discussed by Kornmesser et al. in Fortschr. Röntgenstr. 147: 550–556 (1987) and by Tiling et al. supra.

The use of positive contrast media does to some extent enhance the MR images of the bowels by increasing the signal intensity from solid and liquid bowel contents so enabling the bowels to be more easily distinguished from adjacent body tissues. However, this increased signal intensity carries a double penalty since the signal from gas filled segments is not enhanced and these will therefore show up black in the images and since movements of high signal intensity bowel segments or contents can give rise to problems with ghost artifacts in the images.

The use of negative contrast media for MR imaging of the GI tract has also been suggested. These negative contrast media contain materials whose effect of reducing the spin-spin relaxation time (T2) of the imaging nuclei outweighs any T1 reducing effect and results in a reduction in MR signal intensity from the body regions into which they distribute. Negative contrast media generally contain ferromagnetic, ferrimagnetic or superparamagnetic particles.

The present invention is particularly concerned with contrast media containing particles having ferromagnetic, ferrimagnetic or superparamagnetic properties (hereinafter-referred to as "magnetically responsive particles").

Various different negative contrast media have been proposed for use in MR imaging in general—see for example WO85/4330 (Jacobsen), WO85/02772 and WO89/03675 (Schröder), US-A-4675173 (Widder), DE-A-3443252 (Gries), US-A-4770183 (Groman), L önnemark et al. Acta Radiologica 30:193–196 (1989) Fasc 2, Laniado et al. Fortschr. R öntgenstr. 147:325–332 (1987), Widder et al. AJR 148:399–404 (1987), Mendonca Dias et al. and Olsson et al. SMRM, London, 1985, Edelmen et al. and Williams et al. Radiology 161(P): 314 (1986), Hahn et al. SMRM, Montreal 1986, Book of Abstracts 1537–1538, Hahn et al. Radiology 164:37 (1987), L önnemark et al. Acta Radiologica 29: 599 (1988) and Widder et al. AJR 149:839 (1987) and references therein.

However, while the MR imaging of the GI tract using negative contrast media has been carried out fairly successfully with anaesthetized animals where peristalsis is partially or fully suppressed (see L önnemark et al. Acta Radiologica 29:599 (1988)), imaging with humans remains problematical. Thus, it is usually difficult to achieve satisfactory distribution of the contrast medium in the bowel loops and using concentrations of magnetically responsive particles sufficient to produce the necessary contrast effect throughout the imaged zone can result in the local concentration of magnetically responsive particles in certain regions becoming so high as to produce image distortions akin to "metal artifacts". This is highly undesirable as such artifacts might be mistaken for pathological structures and since the most important function of the contrast medium in such imaging is to allow reliable differentiation between the body cavity, e.g. bowel loop, containing the contrast medium and pathological structures in the body, particularly in the abdomen. Any such uncertainty seriously reduces the diagnostic value of the technique.

As a result, while magnetically responsive particles are extremely effective in enhancing image contrast, several workers have concluded that negative contrast media are of little value or of less value than positive contrast media in abdominal imaging—see for example Laniado et al. supra.

However, we have now surprisingly found that negative contrast media suitable for imaging externally voided body cavities, for example the uterus and the bladder, but especially the GI tract, may be produced by the incorporation of a viscosity enhancing agent that reaches its full viscosity enhancing effect only after administration of the contrast medium.

Thus, in one aspect the present invention provides a contrast medium composition comprising magnetically responsive particles and a physiologically tolerable viscosity enhancing agent for administration with said viscosity enhancing agent incompletely hydrated.

By incompletely hydrated, it is meant that the viscosity enhancing agent is in a form capable of increasing the viscosity of the composition on exposure to aqueous media, e.g. water or body fluids such as gastric juices.

Using the compositions of the invention, identification of the body cavities, e.g. bowel loops, is by identification of low intensity or no intensity regions of the MR image. For this to be achieved the bowel segments (or other cavities) should be filled with the negative contrast medium and to achieve this the gut contents are given increased volume and bulk by the inclusion within the contrast medium of viscosity enhancing or bulking agents. However, ingestion or infusion of large volumes of highly viscous suspensions or gels is difficult or impossible for the patient and preparation of highly viscous contrast media in "ready-to-use" form is also difficult. These problems are overcome according to the present invention by the use of compositions which can be administered before the viscosity enhancing agent has brought the contrast medium up to its maximum viscosity or even up to a viscosity level at which ingestion is uncomfortable.

Thus, in one particularly preferred embodiment, the composition of the invention simply comprises a pulverulent mixture, e.g. a powder or granulate, comprising magnetically responsive particles and a viscosity enhancing agent.

This mixture can simply be dispersed in an aqueous medium, e.g. water, juice or the like, before administration, e.g. by ingestion or infusion. On dispersion in the aqueous medium the viscosity of the medium will increase as the viscosity enhancing agent hydrates, thus enabling the liquid composition to be administered before maximum viscosity is reached. This is important as in this way it is possible to administer compositions whose eventual maximum viscosity is beyond the ability of the patient to ingest or is so high as to make infusion through a tube or catheter impracticable.

In an alternative embodiment, some or all of the viscosity enhancing agent in the compositions of the invention may be provided with a delayed release coating, for example one of the materials available from R öhm GmbH of Darmstadt under the trade name EUDRAGIT, which will release the viscosity enhancing agent only after administration, the release occurring for example in the stomach or on passage into the intestines. Thus, for imaging of the GI tract immediately following the stomach, it may be appropriate to coat the viscosity enhancing agent with an acid soluble coating which will dissolve away in the stomach. Such coatings, and gastric juice resistant coatings which will release the viscosity enhancing agent only on entry into the intestines are well known in the pharmaceutical formulation field.

In this alternative embodiment, the composition of the invention may also be in pulverulent form, but more conveniently it may be in the form of a dispersion or suspension in a physiologically tolerable carrier fluid, e.g. an aqueous fluid, in which the delayed release coating is stable, i.e. does not dissolve.

Using the compositions of the invention, the contrast medium is permitted to develop the desired viscosity at or during passage towards the site which is to be imaged, e.g. the bowels.

Thus for example, using compositions according to the invention, it is possible for the patient to ingest the contrast medium in the dosage volumes usually required for oral contrast agents, e.g. 300–1000 ml, while the medium is still at a sufficiently low viscosity to be swallowed and yet for the medium to develop to its maximum or desired viscosity before imaging is effected due to the time required for the medium to pass down the gastrointestinal tract. The viscosity which develops within the medium secures an even distribution of the magnetically responsive particles in the portion of the gastrointestinal tract that is to be imaged, and thus permits effective imaging of that portion.

In the case of compositions capable of developing particularly high viscosities, the viscosity that is developed may even serve to slow the passage of the contrast medium through the bowels, and this retarded passage can, if desired, be used to keep the contrast medium in regions such as the duodenum through which passage is normally quite rapid.

The viscosity enhancing agent in the compositions of the invention should be a material capable of maintaining high viscosity levels at the conditions of the body cavity which is to be imaged and thus preferably is a non-biodegradable material, especially where the composition is intended for oral ingestion. The viscosity enhancing agent may conveniently be a material which is soluble in aqueous media to produce a viscous solution. Examples of such materials include natural, semi-synthetic and synthetic high molecular weight substances such as, for example, natural or semi synthetic gums and polysaccharides, e.g. guar gum, tragacanth, methylcellulose, hydroxypropyl cellulose, carboxymethyl cellulose, xanthan gum, alginates and, where applicable, their physiologically acceptable salts. Many examples of such materials are known as thickening agents in the food industry.

Alternative viscosity enhancing agents include insoluble materials which swell in aqueous media to produce viscous dispersions. Typical examples of such swellable viscosity enhancing agents include clays, e.g. kaolin, and related minerals such as, for example, magnesium aluminium silicate, bentonite, etc. Mixtures of Soluble and insoluble viscosity enhancing agents can of course also be used.

Bulking agents such as those used in the treatment of constipation such as bran, psyllium and methyl cellulose may also be used as viscosity enhancing agents or in combination with further viscosity enhancing agents for compositions according to the invention for administration into the GI tract.

Where the viscosity enhancing agent in the composition of the invention is in particulate form, and especially where it is a water-swellable agent, the rate of increase of viscosity of the contrast medium will, of course, be strongly dependent on the particle size. As is well known, smaller particles hydrate relatively more rapidly than larger particles.

Thus the concentration, physical form and chemical nature of the viscosity enhancing agent in the compositions of the invention can conveniently be matched to the end use of the contrast medium to enable viscosity development to be sufficiently slow to permit the composition to be administered in a relatively low viscosity form and yet sufficiently fast as to ensure that the desired viscosity level has been reached when imaging of the body cavity containing the contrast medium takes place. It will, of course, be realised that for different body cavities or different segments of the GI tract the optimal viscosity of the contrast medium will differ. Thus for the colon relatively low viscosity levels and for the oesophagus relatively high viscosity levels may advantageously be used. After hydration of the viscosity enhancing agent, the compositions of the invention will generally have viscosities of 200 to 5000 cps, especially 300 to 4000 cps, but for certain uses viscosities may be greater, e.g. up to 150000 cps or even higher.

In general, where the composition is in pulverulent form for mixing with water or juice or another aqueous medium before administration, the viscosity enhancing agent should be such that the maximum viscosity acceptable for administration is reached between 15 seconds and 60 minutes, preferably between 1 and 30 minutes, especially preferably between 2 and 10 minutes, after contacting the viscosity enhancing agent with the aqueous medium. Where the contrast medium has to be ingested or infused in large quantities, e.g. 500 ml or more, or where it has to be administered through a narrow tube or to a patient experiencing problems with swallowing, it is especially preferred that the medium should not become too viscous too quickly so that the full quantity of contrast medium can be administered.

Thus, the content and nature of viscosity enhancing agent in the composition of the invention is conveniently such that for at least 15 seconds, preferably at least 2 minutes and especially preferably at least 5 minutes, following mixing (or on administration where mixing is not required) the contrast medium should have a viscosity of less than 1000 cps, preferably less than 700 cps, more preferably less than 300 cps, especially preferably less than 200 cps, and such that in due course, e.g. within 15 60 minutes, or on dissolution of any delayed release coating, the viscosity of the medium should increase to an adequate level for imaging of the desired body cavity. Thus, for example, the viscosity of the medium may increase to at least 500 cps, preferably at least 1000 cps, especially at least 2000 cps, e.g. 600 to 5000 cps, preferably 1500 to 4000 cps. As mentioned above, even higher viscosities may be desirable for imaging certain body cavities or GI tract segments, e.g. up to 150000 cps or even higher.

The viscosity of the compositions of the invention before, during or after mixing can conveniently be measured at 20° C. using a Brookfield viscometer.

The absolute concentration of the viscosity enhancing agent in the compositions of the invention is thus clearly dependent on whether or not the composition is in liquid form ready for administration and on the chemical nature of the individual agent used, and on the dilution ratio where the composition is intended to be dispersed in water or another aqueous medium before administration. It may however be selected on the basis of the known properties of the agent, or with minimal routine experimentation. However, in general the viscosity enhancing agent will conveniently constitute from 1 to 99.5% especially 8 to 98% by weight of the composition of the invention.

The compositions of the invention also include magnetically responsive particles, the components actually responsible for the negative MRI contrast.

As mentioned above, many forms of magnetically responsive particle have been proposed for use as MRI contrast agents and generally speaking, all such particles may be used in the compositions of the invention. Thus the particles may be free or may be coated by or embedded in or oneparticles of a non-magnetic carrier material, e.g. a natural or synthetic polymer, for example cellulose or a sulphonated styrene-divinyl benzene copolymer (see for example WO83/03920 of Ugelstad). The magnetically responsive particles may be ferromagnetic or ferrimagnetic or may be sufficiently small as to be superparamagnetic and indeed superparamagnetic particles are generally preferred.

Thus the magnetically responsive particles used according to the present invention may be of any material which (although preferably non-radioactive unless the particles are also intended to be detected by their radioactive decay emissions) exhibits ferromagnetism, ferrimagnetism or superparamagnetism. The particles may conveniently be particles of a magnetic metal or alloy, e.g. of pure iron, but particularly preferably will be of a magnetic compound such as a ferrite, for example magnetite, gamma ferric oxide and cobalt, nickel or manganese ferrites.

Particles such as those described by Ugelstad in WO83/03920, by Schröder in WO83/01738, WO85/02772 and WO89/03675, by Molday in US-A-4452773, by Widder in US-A-4675173 and by Groman in WO88/00060 and US-A-4770183 or those such as Biomag M4200 available from Advanced Magnetics Inc. of Cambridge, Mass. U.S.A., are particularly suitable for use in the compositions of the invention.

To avoid image distortion, it is preferred that the mean particle size of the magnetically responsive particles be less than about 5 micrometers, preferably less than 1 micrometer and that the overall size of the non-magnetic carrier particles be less than 50 micrometers, preferably less than 20 micrometers, especially preferably 0.1 to 5 micrometers. The magnetically responsive particles will generally have mean particle sizes in the range 0.002 to 1 micrometers, preferably 0.005 to 0.2 micrometers.

Where the magnetically responsive particles are carried by carrier particles, these are preferably of a material which is physiologically tolerable and which is not biodegradable, at least in the enviroments it will experience on the way to and at the body cavity being imaged.

The composition of the invention may, of course, include components other than the viscosity enhancing agent and the magnetic particles, for example conventional pharmaceutical formulation aids such as wetting agents, disintegrants, binders, fillers, osmoactive agents, flavouring agents and, where the composition is not in dry form, liquid carrier media. However, to improve contact between the magnetically responsive particles and the walls of the body cavity, e.g. the gut wall, the compositions may also contain mucoadhesives, such as for example a polyacrylic acid or a derivative thereof, xanthan gum, etc.

The compositions of the invention are particularly suited to use, if necessary after dispersion in aqueous media, as MRI contrast media for imaging of the gastrointestinal tract and in particular for imaging the duodenum and the intestines. For such a purpose the contrast medium may be administered orally or rectally or by orally or rectally inserted tubes. However, as indicated above the contrast media are of course also suitable for use in imaging other externally voided body cavities such as the bladder, uterus and vagina.

Thus viewed from another aspect the present invention provides the use of a physiologically tolerable viscosity enhancing agent for the manufacture of a composition for use in magnetic resonance imaging.

Viewed from yet another aspect the present invention provides the use of magnetically responsive particles for the manufacture of a composition for use in magnetic resonance imaging.

Thus, viewed from a further aspect the present invention provides a method of generating a magnetic resonance image of a human or non-human, e.g. mammalian, subject in which method a contrast medium comprising magnetically responsive particles and a viscosity enhancing agent is administered into an externally voided body cavity of said subject (e.g. the gastrointestinal tract), wherein said viscosity enhancing agent acts to increase the viscosity of said medium following administration of said medium into said subject.

Viewed from a yet further aspect the present invention provides a diagnostic contrast agent kit comprising a plurality of magnetically responsive particles and, packaged separately thereto, a physiologically tolerable viscosity enhancement agent in pulverulent form.

In the method of the invention it is possible to formulate the contrast medium immediately or shortly before administration by mixing a viscosity enhancing agent with the magnetically responsive particles (which may already be dispersed in an aqueous carrier medium) and thus in a further aspect the invention also provides an MRI contrast agent kit comprising in a first container a plurality of magnetically responsive particles optionally dispersed in an aqueous carrier medium, and in a second container a viscosity enhancing agent for admixture to said particles.

In the method of the invention the dose of the contrast medium will generally be at least 30 ml for an adult human subject and more usually 200 to 1500 ml, especially 300 to 1000 ml. In this the content of the magnetically responsive particles will depend on the particular particles used. However, the particles will generally be contained at a concentration of 0.01 to 10 g/liter, preferably 0.1 to 3 g/liter. The dose may be taken in portions, e.g. for oral administration about ⅔ being ingested 20 minutes before imaging and the remainder being ingested immediately before the subject is placed on the imager. The portions can of course be mixed in separate batches.

The invention is further illustrated by the following non-limiting examples:

EXAMPLE 1

| | |
|---|---|
| Microcrystalline cellulose | 2500 g |
| Xanthan gum | 500 g |
| Corn starch | 1500 g |
| Aspartame | 15 g |

The substances are dry blended and granulated with a granulating liquid of the following composition:

| | |
|---|---|
| Polyvinyl pyrrolidone | 200 g |
| Magnetic particles* | 35 g |
| Purified water | 1800 g |

*The magnetic particles consist of small superparamagnetic crystals <50 nm of magnetite coated on to a polymer carrier matrix consisting of monodisperse particles having a diameter of 3.5 micrometers. The iron content is approximately 20% by weight. The particles are produced by the method of Ugelstad supra.

The granulate is dried and screened to give a granulate fraction of 0.3 to 1.5 mm. Before administration 10 g of the granulate suspended in 100 ml water will give a viscosity of approximately 2500 cps when fully hydrated. For at least three minutes from suspension the viscosity remains sufficiently low (less than about 200 cps) for easy administration, e.g. by ingestion.

* The magnetic particles consist of small superparamagnetic crystals <50 nm of magnetite coated on to a polymer carrier matrix consisting of monodisperse particles having a diameter of 3.5 micrometers. The iron content is approximately 20% by weight. The particles are produced by the method of Ugelstad supra.

EXAMPLE 2

| | |
|---|---|
| Microcrystalline cellulose | 2500 g |
| Xanthan gum | 500 g |
| Corn starch | 1500 g |
| Aspartame | 15 g |

These substances are dry blended and granulated with a granulating liquid of the following composition:

| | |
|---|---|
| Polyvinyl pyrrolidone | 200 g |
| Purified water | 1800 g |

The granulate is dried and screened to give a granulate fraction of 0.3 to 1.5 mm. Before administration 10 g of the granulate is mixed with 100 ml of an aqueous suspension of 50 mg magnetic particles (see Example 1). When fully hydrated the viscosity will be approximately 2500 cps.

EXAMPLE 3

| | |
|---|---|
| Xanthan gum | 1500 g |
| Lactose | 3500 g |

These substances are dry blended and granulated with a granulating liquid of the following composition:

| | |
|---|---|
| Polyvinyl pyrrolidone | 75 g |
| Ethanol | 900 g |
| Purified water | 900 g |
| Magnetic particles* | 35 g |

*see Example 1

The granulate is dried and screened to give a granulate fraction of 0.3 to 1.5 mm. Before administration 7 g of the granulate is suspended in 100 ml of water. Fully hydrated the contrast medium will have a viscosity of about 2000 cps.

EXAMPLE 4

| Microcrystalline cellulose | 2000 g |
|---|---|
| Xanthan gum | 500 g |
| Carboxymethyl cellulose sodium | 500 g |
| Lactose | 1500 g |

These substances are dry blended and granulated with a granulating liquid of the following composition:

| Polyvinyl pyrrolidone | 200 g |
|---|---|
| Purified water | 2000 g |
| Magnetic particles* | 35 g |

*see Example 1

The granulate is dried and screened to give a granulate fraction of 0.3 to 1.5 mm. Before administration 10 g of the granulate is suspended in 100 ml water. If taken within 3 minutes the contrast medium will be easily ingested. Fully hydrated the viscosity will be approximately 2300 cps.

EXAMPLE 5

| Microcrystalline cellulose | 2000 g |
|---|---|
| Xanthan gum | 500 g |
| Corn starch | 1500 g |
| Aspartame | 15 g |

These substances are dry blended and granulated with a granulating liquid of the following composition:

| Polyvinyl pyrrolidone | 200 g |
|---|---|
| Purified water | 2000 g |
| Magnetic particles* | 80 g |

*see Example 1

The granulate is dried and screened to give a granulate fraction of 0.3 to 1.5 mm. Before use 3 g of the granulate are suspended in 100 ml water. The contrast medium will have a viscosity of approximately 600 cps when fully hydrated. The medium however is ingested before hydration is complete.

I claim:

1. A contrast medium composition for administration to a patient for MR imaging comprising a pulverulent mixture of superparamagnetic, ferrimagnetic or ferromagnetic particles together with a physiologically tolerable viscosity enhancing agent, such that following dispersion of said composition in a physiologically tolerable carrier fluid it may be administered to said patient with the viscosity of the composition increasing after such administration.

2. A composition as claimed in claim 1 comprising a said viscosity enhancing agent provided with a delayed release coating.

3. A composition as claimed in claim 2 comprising a said viscosity enhancing agent provided with a gastric fluid-resistant delayed release coating.

4. A composition as claimed in claim 1 wherein said viscosity enhancing agent is non-biodegradable.

5. A composition as claimed in claim 1 wherein said viscosity enhancing agent is water-soluble, water-swellable, or is a bulking agent, or comprises a mixture of such materials.

6. A composition as claimed in claim 1, wherein said viscosity enhancing agent achieves a viscosity of 200–500 cps upon hydration.

7. A composition as claimed in claim 1, wherein said viscosity enhancing agent achieves a maximum viscosity within 15 seconds to 60 minutes of contact with an aqueous medium.

8. A composition as claimed in claim 1, wherein said viscosity enhancing agent achieves a maximum viscosity after at least two minutes of contact with an aqueous medium.

9. A composition as claimed in claim 1, wherein said viscosity enhancing agent constitutes 1 to 99.5% by weight of the composition.

10. A composition as claimed in claim 1, wherein said magnetically responsive particles are selected from particles of magnetite, gamma ferric oxide, and cobalt, nickel and manganese ferrites.

11. A method of generating a magnetic resonance image of a human or non-human animal body, said method comprising administering to an externally voided body cavity of said body a composition as claimed in claim 1, after dispersion thereof in a physiologically tolerable aqueous medium and before complete hydration of the viscosity enhancing agent therein, and generating a magnetic resonance image of at least part of said body.

12. A diagnostic contrast agent kit comprising a plurality of superparamagnetic, ferrimagnetic or ferromagnetic particles and, packaged separately thereto, a physiologically tolerable viscosity enhancing agent in pulverulent form.

* * * * *